(12) United States Patent
Tuvim

(10) Patent No.: US 6,527,951 B1
(45) Date of Patent: Mar. 4, 2003

(54) CHROMATOGRAPHIC COLUMN

(75) Inventor: Yuri Tuvim, Newton, MA (US)

(73) Assignee: Waters Investments Limited

( * ) Notice: Subject to any disclaimer, the term of this patent is extended or adjusted under 35 U.S.C. 154(b) by 96 days.

(21) Appl. No.: 09/714,662

(22) Filed: Nov. 16, 2000

(51) Int. Cl.[7] .............................................. B01D 15/08
(52) U.S. Cl. .................... 210/198.2; 210/450; 210/456; 96/101; 96/107
(58) Field of Search .............................. 210/656, 198.2, 210/232, 450, 456, 541; 96/101, 105, 107

(56) References Cited

U.S. PATENT DOCUMENTS

| | | | |
|---|---|---|---|
| 4,026,803 A | 5/1977 | Abrahams et al. | 210/198.2 |
| 4,457,846 A | 7/1984 | Munk | 210/198.2 |
| RE31,974 E | 8/1985 | Brownlee | 210/198.2 |
| 4,550,594 A | 11/1985 | Engstrom | 210/198.2 |
| 4,692,243 A | 9/1987 | Prosch et al. | 210/198.2 |
| 5,089,125 A * | 2/1992 | Hart | 210/198.2 |
| 5,137,628 A | 8/1992 | Hart | 210/198.2 |

* cited by examiner

*Primary Examiner*—Ernest G. Therkorn
(74) *Attorney, Agent, or Firm*—Brian Michaelis; Anthony J. Janiuk

(57) ABSTRACT

A chromatography column with filters having minimal volume. A stamped screen disk is coated with fluorocarbon polymer on both sides, leaving a center area open. The fluorocarbon polymer coating serves as a gasket, providing reliable sealing for pressure up to approximately 10000 psi. The chromatography column comprises a fitting having an internal cavity. A fluorocarbon polymer coated screen is placed within the cavity. A threaded capillary tubing is screwed inside the cavity. At the end of the capillary lies a compression screw solvent tubing connection.

10 Claims, 2 Drawing Sheets

CHROMATOGRAPHIC COLUMN

FIELD OF THE INVENTION

The present invention relates to chromatographic columns, especially capillary columns.

BACKGROUND OF THE INVENTION

Liquid chromatography systems are used to carry out chemical separations. A typical liquid chromatography system consists of the following major components: a pump, an injector, a column, and a detector. The pump compels a mobile phase, for example, a solution, through a fluid path comprising an injector, column and a detector. The injector permits the introduction of samples into the fluid stream above the column. The column contains a packed bed of media. The media is normally porous and relatively inert. Compounds in the sample will exhibit a characteristic affinity to the media. That is, some compounds exhibit high affinity and some compounds exhibit low affinity. As a result, as the compounds are carried through the media, the compounds separate into bands which elute or come off the column at different times. These bands are detected by the detector.

The media within a column is held in place by filters or frits. The filters or frits are secured in the column by end caps. The volume of the column's filters or frits greatly affects the performance of the chromatography system. It is desirable to minimize volume of the chromatograph system. Once removed from the media and the influence of affinity thereto, compounds tend to redistribute in solution. The smaller the volume of a column's filters or frits, the better the column performs. Small volume columns tend to use filters, as opposed to frits. In a capillary column, which volume is measured in microliters, the volume of the filters is especially important.

There are numerous manufacturers offering filter assemblies for chromatographic columns (Upchurch Scientific, Isolation Technologies, Optimize Technologies, Merck, Alltech and others). The smallest thickness of all available filters is 0.75 micron. It would be advantageous to have a thinner filter because its volume would be smaller.

Existing powder metallurgy technology cannot provide parts thinner than 0.25 micron. Filters and frits of that thickness cannot be reliably pressed into thin plastic rings typically used to seal and retain the frits and filters in the column.

SUMMARY OF THE INVENTION

The present invention provides a chromatography column with filters or frits having minimal volume. One embodiment of the present invention is directed to a chromatography column for use with a chromatographic pump having a solute conduit. The column comprises a cylindrical tube having a cylindrical wall having a interior surface, an exterior surface, a first face and a second face. The interior surface defines a chamber. The first and second faces are between the interior and exterior surfaces, and with the interior surface, define two openings to said chamber. At least one of the first and second faces has a circular planar surface for receiving a filter element. The circular planar surface has an inside diameter and an exterior diameter. A filter element is received on the flat planar surface of the face. The filter element has a screen having a top surface, a bottom surface, and a diameter greater than the diameter of the inside diameter of the circular planar surface. The screen has a coating of a plastic material. The plastic material is positioned on the screen in a circular ring defining an area substantially free of the plastic material in the center of the screen. The plastic material engages the flat planar surface in sealing engagement upon compression upon the top surface. The column further comprises at least one end-fitting assembly at one of the faces. The end fitting assembly has a fitting body having a tube opening for receiving the exterior wall of the tube. The tube opening has a lip extending radially inward to form a retaining surface. The retaining surface receives the filter element and engages the coating in sealing relationship upon compression. The lip defines a lip opening having a diameter greater than the diameter of the solute conduit, for receiving the solute conduit in sealing engagement with the coating of the filter element upon compression. The end fitting assembly receives a solute conduit and places the chamber in fluid communication with a chromatographic solute through the filter element.

As used herein, the term filter element means a filter or frit. Preferably, the filter element is formed of stainless steel screen, sintered stainless steel frit, or membrane. Preferably, the coating is fluorocarbon polymer. Fluorocarbon polymers such as PTFE, FEP or PVDF are sold by a variety of vendors. A preferred fluorocarbon polymer is sold under the trademark "TEFLON" (Du Pont).

The chromatography column filter element of the present invention provides several benefits over conventional columns filters and frits. The chromatography column equipped with this filter element has minimal dead volume. The properties of the fluorocarbon surfaces create a sealing gasket that dispenses with the need for additional sealing rings. It does not require precisely machined parts. The chromatography column can be reliably sealed. One embodiment of the filter element is a stamped screen disk which is coated with a fluorocarbon polymer on both sides, leaving a center area open. The coating serves as a gasket, providing reliable seal.

Preferably, the fitting body and cylindrical tube have cooperating threads to provide compression of said coating.

Preferably, the lip opening of the fitting body has a cylindrical section proximal to the filter element for receiving the solute conduit, a conical section expanding from the cylindrical section for receiving a cooperating conical section of a sleeve assembly, and a cylindrical section. The end fitting assembly further comprises a sleeve assembly comprising a ferrule and a compression screw. The ferrule and compression screw have axial openings for receiving the solute conduit. The ferrule and compression screw are configured and arranged to cooperate with the conical and cylindrical sections of the fitting body. The conical section of the fitting body compresses the ferrule and solute conduit as the ferrule is received in the conical section of the fitting body. The ferrule engages the conical section of the fitting body to seal the solute conduit against the ferrule and the ferrule against the end-fitting body.

Preferably, the compression screw further comprises a cylindrical section to cooperate the cylindrical section of the fitting body. The fitting body cylindrical section and the compression screw cylindrical section have cooperating threads to provide compression on the ferrule. The ferrule engages the solute conduit to compel the conduit against the filter element in sealing engagement with the coating.

Typical chromatography columns are packed with a solid phase media, such as particles of silica oxide, titanium oxide, zirconium oxide, carbon, hydrocarbon polymeric material, and combinations thereof. The filter element serves to contain such material. Preferably there are at least two filter elements and end fitting assemblies.

BRIEF DESCRIPTION OF THE DRAWINGS

The foregoing and other features and advantages of the present invention will be more fully understood from the following detailed description of illustrative embodiments, taken in conjunction with the accompanying drawings in which:

FIG. 2b is an enlargement of a portion A of FIG. 2a.

DETAILED DESCRIPTION OF THE INVENTION

Figure 1:
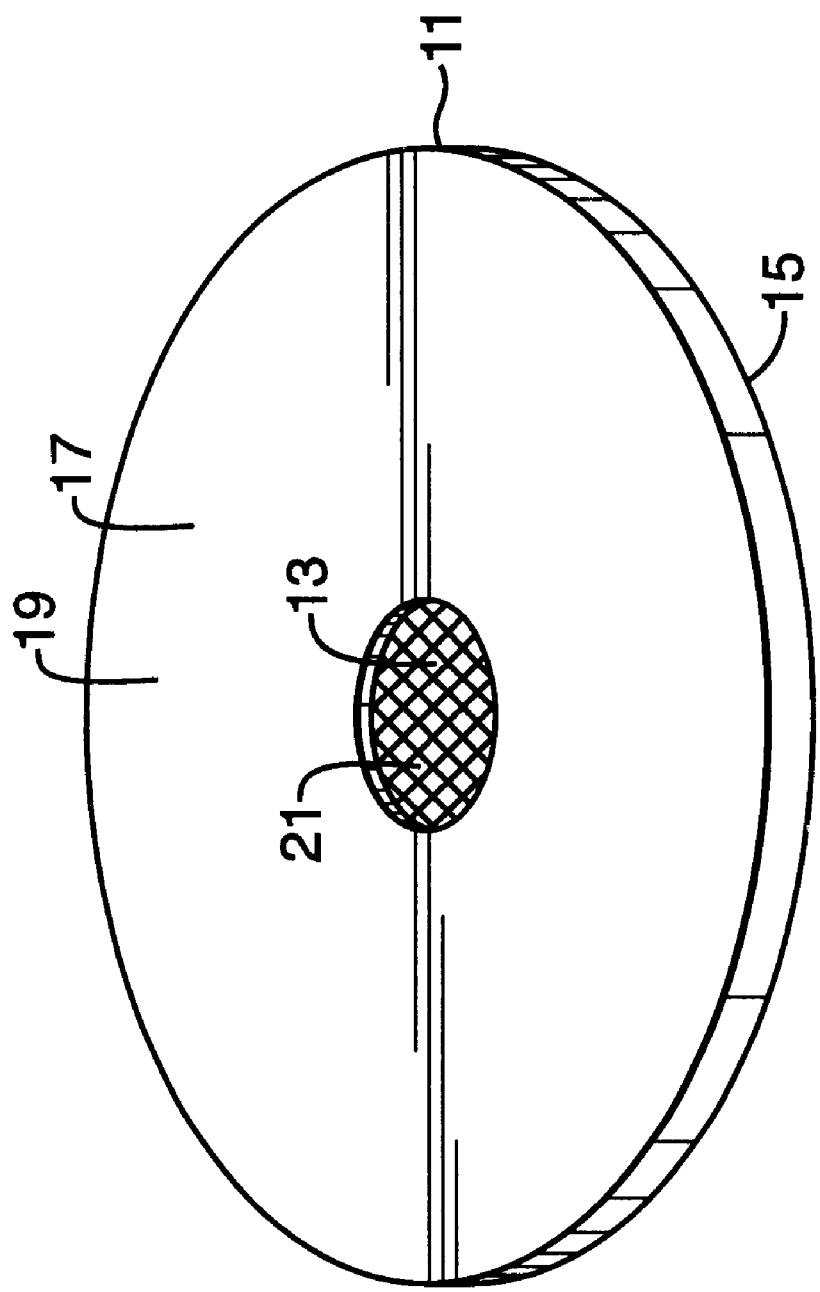
FIG. 1 illustrates a column filter according to the present invention.

Referring in detail to the drawings, the chromatographic filter element 11 of the present invention is shown in perspective in FIG. 1. It comprises a circular screen 13 that is coated on both a bottom surface 15 and a top surface 17 with a plastic material 19. A preferred plastic material 19 is a fluorocarbon polymer. Fluorocarbon polymers are known to be relatively chemically inert. Fluorocarbon polymers such as PTFE, FEP or PVDF are sold by a variety of vendors. A preferred fluorocarbon polymer is sold under the trademark "TEFLON" (Du Pont).

The coating is applied or removed leaving a center area 21 open for fluid passage. The circular screen 13 is coated with a fluorocarbon polymer to form a ring of plastic material or gasket that allows reliable sealing when the filter element 11 is placed within the end fittings 23, as described hereinafter with reference to FIGS. 2a and 2b.

Circular screen 13, as shown in FIG. 1, in the illustrative embodiment, is fabricated from a stainless steel screen that is capable of trapping particles as small as approximately 2 microns. The screen 13 is a stamped circular section of stainless steel screen having a thickness of between 90 to 140 microns.

In an alternative embodiment a sintered stainless steel frit can be used; and, other materials known in the art may be utilized, provided that the material is inert to the sample substance and solvents utilized. In the event the coating 19 is placed on the entire screen 13, a circular area 21 of the screen 13 can be formed by removing the coating 19 with a carbon dioxide laser. In the alternative, a mask [not shown] can be placed on the screen 13 prior to applying the coating 19. After the coating 19 is applied, the mask is removed to expose area 21.

Figure 2A:
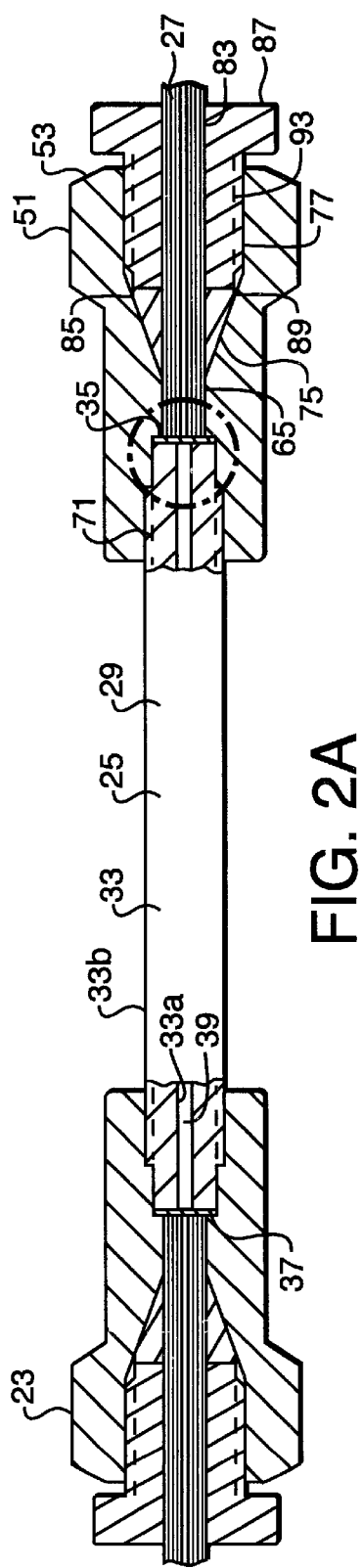
FIG. 2a shows a capillary chromatography column according to the present invention.
Figure 2B:
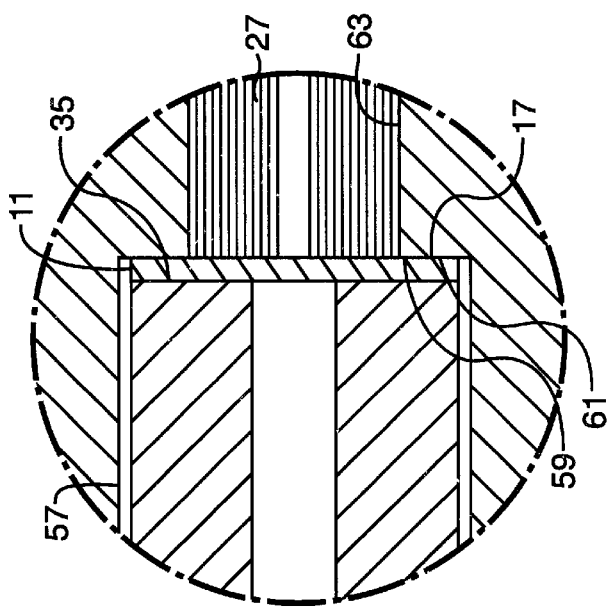

Referring now to FIGS. 2a and 2b, one embodiment of the present invention is directed to a chromatography column, generally designated by the numeral 25. The column 25 comprises a cylindrical tube 29 having a cylindrical wall 33 having a interior surface 33a, an exterior surface 33b, a first face 35 and a second face 37.

The interior surface 33a defines a chamber 39. The first and second faces 35 and 37 are between the interior and exterior surfaces 33a and 33b respectively. And, such faces 35 and 37, with the interior surface 33a, define two openings to the chamber 39. Chamber 39 is typically packed with a solid phase media [not shown for purposes of clarity]. This media can take any number of forms known in the art. Typical chromatography columns are packed with particles of silica oxide, titanium oxide, zirconium oxide, carbon, hydrocarbon polymeric material, and combinations thereof. The filter element 11 serves to contain such material. Preferably there are at least two filter elements 11.

At least one of the first and second faces 35 and 37 has a circular planar surface 41 for receiving a filter element 11. The circular planar surface 41 has an inside diameter and an exterior diameter.

Turning now to FIG. 2b in particular, a filter element 11 is received on the flat planar surface 41 of the face 35. The filter element 11 has a top surface 15, a bottom surface 17, and a diameter greater than the inside diameter of the circular planar surface 41. The filter element 11 has a coating of a plastic material 19. The plastic material 19 is positioned on the screen 13 in a circular ring, defining an area 21 substantially free of the plastic material 19, in the center of said screen 13. The plastic material 19 engages the flat planar surface 41 in sealing engagement upon compression upon said top surface 15.

The column 25 further comprises at least one end-fitting assembly 51, and preferably two. Each end fitting assembly is positioned at one of the faces 35 and 37. The end fitting assembly 51 has a fitting body 53 having a tube opening 57 for receiving the exterior wall 33b of the tube 33. The tube opening 57 has a lip 59 extending radially inward to form a retaining surface 61. The retaining surface 61 receives the filter element 11 and engages the coating 19 in sealing relationship upon compression. The lip 59 defines a lip opening 63 having a diameter greater than the diameter of the solute conduit 27, for receiving the solute conduit 27 in sealing engagement with the filter element 11 on the coating 14 upon compression. The one end fitting 51 receives a solute conduit 27 and places the chamber 39 in fluid communication with a chromatographic solute through the filter element 11.

The chromatography column filter of the present invention provides several benefits over conventional columns filters. The chromatography column equipped with this filter has minimal dead volume. The properties of the fluorocarbon surfaces create a sealing gasket that dispenses with the need for additional sealing rings. It does not require precisely machined parts. The chromatography column can be reliably sealed. The fluorocarbon coating serves as a gasket, providing reliable sealing for pressure up to approximately 10,000 psi.

Preferably, the fitting body 53 and cylindrical tube 25 have cooperating threads 71 to provide compression of said coating 19. In the alternative, the tube 25 can be fitted into the fitting body 53, compressing the coating 19, and secured in place by gluing, welding, brazing and crimping.

Preferably, the lip opening 63 of the fitting body 53 has a cylindrical section 65 proximal to the filter element 11 for receiving the solute conduit 27, a conical section 75 expanding from the cylindrical section 65 for receiving a cooperating conical section of a sleeve assembly, and end cylindrical section 77. The end fitting assembly further comprises a sleeve assembly 81 comprising a compression screw 87 and a ferrule 89.

Compression screw 87 has an axial opening 83 for receiving the solute conduit 27. Compression screw 87 has a flat section 85 configured and arranged to cooperate with ferrule 89. The flat section 85 of the compression screw 87 compresses the ferrule 89 as the ferrule 89 engages the conical section 75 of the fitting body 53. The ferrule 89 compresses the solute conduit 27 to seal the solute conduit 27 against the ferrule 89 and the ferrule 89 against the fitting body 53.

Preferably, the compression screw 89 further comprises a cylindrical section 87 and the fitting body has a cylindrical section 91. The fitting body cylindrical section 91 and the sleeve cylindrical section 87 have cooperating threads 93 to provide compression on the sleeve body 87. The sleeve body 87 engages the solute conduit 27 to compel the conduit against the filter element 11 in sealing engagement with the coating 19.

In the alternative, the sleeve assembly 87 can be forced against the fitting body 53 and fixed by gluing, welding, brazing and crimping.

Embodiments of the present invention feature a chromatography column having a small dead volume. That is the distance between the solute conduit and the filter element 11 is minimal. The filter element of the present invention can withstand pressures of approximately 10,000 psi within the chromatographic apparatus. The properties of the coating 19 creates a sealing gasket that dispenses with the need for additional sealing rings within the apparatus and thus decreases the need for additional components in the form of sealing structure. The incorporation of the sealing structure and the filtering structure into a singular component provides the user with a more efficient column with fewer precision dimensioned parts.

As disclosed herein, the invention provides a new method and apparatus in the form of a sealed chromatography column that integrates the sealing structure within the structure of the filter assembly. This design allows for a greater reliability of the sealing of the above columns and maximizes the performance of the column. While the sealing arrangement integrated within the filter of the present invention can be used in virtually any size chromatography column and for virtually any column pressure up to approximately 10,000 psi, it is particularly well suited to capillary applications. Additionally, the simplicity of the design of the above filter with integrated sealing greatly enhances the reliability and performance of the column.

Although the filter material described in the illustrative embodiment herein is a stainless steel screen it should be appreciated that other filters could be implemented such as sintered stainless steel frit, or the like. Similarly, rather than a screen, filtering could be effected by making the filtering component from a membrane material that possesses sufficient strength containing pores specific to the needed size.

The foregoing has been a description of an illustrative embodiment of the present invention. While several illustrative details have been set forth, such are only for the purpose of explaining the present invention. Various other changes, omissions and additions in the form and detail thereof may be made therein without departing from the spirit and scope of the invention.

What is claimed is:

1. A chromatography column for use with a chromatographic pump having a solute conduit, comprising:
    a cylindrical tube having a cylindrical wall having a interior surface, an exterior surface, a first face and a second face, said interior surface defining a chamber, said first and second face between said interior and exterior surfaces and with said interior surface, defining two openings to said chamber, at least one of said first and second faces having a circular planar surface for receiving a filter element said circular planar surface having a inside diameter and an exterior diameter;
    a filter element received on said flat planar surface of said at least one face, said filter element having a screen having a top surface, a bottom surface, and a diameter greater than the diameter of said inside diameter of said circular planar surface, said screen having a coating of a plastic material, said plastic material positioned on said screen in a circular ring defining a area substantially free of said plastic material in the center of said screen, said plastic material engaging said flat planar surface in sealing engagement upon compression upon said top surface;
    at least one end-fitting assembly at the said at least one face, said end fitting assembly having a fitting body having a tube opening for receiving said exterior wall of said tube, said tube opening having a lip extending radially inward to receive said filter element on said bottom surface and engage said coating in sealing relationship upon compression, said lip defining an lip opening having a diameter greater than the diameter of said solute conduit for receiving said solute conduit in sealing engagement with said filter element on said coating upon compression;
    said at least one end fitting for receiving a solute conduit and placing said chamber in fluid communication with a chromatographic solute through said filter.

2. The chromatography column according to claim 1, wherein said filter is formed of stainless steel screen.

3. The chromatography column according to claim 1, wherein said filter is formed of sintered stainless steel frit.

4. The chromatography column according to claim 1, wherein said coating is fluorocarbon polymer.

5. The chromatography column according to claim 1, wherein said at least one endfitting assembly fitting body and cylindrical tube have cooperating threads to provide compression of said coating.

6. The chromatography column according to claim 1, wherein said lip opening of said end fitting assembly fitting body has a cylindrical section proximal to said filter for receiving said solute conduit, a conical section expanding from said cylindrical section for receiving a cooperating conical section of a sleeve assembly and a end cylindrical section, said end fitting assembly further comprising a sleeve assembly comprising a ferrule and a compression screw said compression screw and ferrule having an axial opening for receiving said solute conduit and said ferrule having a conical section configured and arranged to cooperate with said conical section of said fitting body, said ferrule compressing said solute conduit as said ferrule engages said conical section of said end fitting assembly body to seal said solute conduit against said ferrule and said ferrule against said end-fitting body.

7. The chromatography column of claim 6 wherein said compression screw further comprises a cylindrical section and said fitting body cylindrical section and said sleeve cylindrical section have cooperating threads to provide compression on said ferrule.

8. The chromatography column of claim 7 wherein said sleeve assembly engages said solute conduit to compel said conduit against said filter in sealing engagement with said coating.

9. The chromatography column according to claim 8 wherein said filter is a membrane.

10. A chromatography column for use with a chromatographic pump having a solute conduit, comprising:
    a cylindrical tube having a cylindrical wall having a interior surface, an exterior surface, a first face and a second face, said interior surface defining a chamber, said first and second face between said interior and exterior surfaces and with said interior surface, defining two openings to said chamber, at least one of said first and second faces having a circular planar surface for receiving a filter element said circular planar surface having a inside diameter and an exterior diameter;

a filter element received on said flat planar surface of said at least one face, said filter element having a screen having a top surface, a bottom surface, and a diameter greater than the diameter of said inside diameter of said circular planar surface, said screen having a coating of a plastic material, said plastic material positioned on said screen in a circular ring defining a area substantially free of said plastic material in the center of said screen, said plastic material engaging said flat planar surface in sealing engagement upon compression upon said top surface;

at least one end-fitting assembly at the said at least one face, said end fitting assembly having a fitting body having a tube opening for receiving said exterior wall of said tube, said tube opening having a lip extending radially inward to receive said filter element on said bottom surface and engage said coating in sealing relationship upon compression, said lip defining a lip opening having a diameter greater than the diameter of said solute conduit for receiving said solute conduit in sealing engagement with said filter element on said coating upon compression; wherein said at least one end-fitting assembly fitting body and cylindrical tube have cooperating threads to provide compression of said coating; and wherein said lip opening of said end fitting assembly fitting body has a cylindrical section proximal to said filter for receiving said solute conduit, a conical section expanding from said cylindrical section for receiving a cooperating conical section of a sleeve and a end cylindrical section, said end fitting assembly further comprising a sleeve assembly comprising a ferrule and a compression screw, said ferrule and compression screw having an axial opening for receiving said solute conduit, said ferrule having a conical section configured and arranged to cooperate with said conical section of said fitting body, said conical section of said ferrule compressing said solute conduit as said ferrule engages said conical section of said end fitting assembly body to seal said solute conduit against said ferrule and said ferrule against said end-fitting body; said compression screw cooperating with said fitting body to provide compressing of said ferrule, said at least one end fitting for receiving a solute conduit and placing said chamber in fluid communication with a chromatographic solute through said filter.

* * * * *